United States Patent
Lee et al.

(10) Patent No.: US 9,345,451 B2
(45) Date of Patent: May 24, 2016

(54) METHOD, APPARATUS, AND SYSTEM FOR MEASURING PROPAGATION OF SHEAR WAVE USING ULTRASOUND TRANSDUCER

(71) Applicant: Samsung Electronics Co., Ltd., Suwon-si (KR)

(72) Inventors: Hyoung-ki Lee, Seongnam-si (KR); Dong-geon Kong, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 287 days.

(21) Appl. No.: 13/903,220

(22) Filed: May 28, 2013

(65) Prior Publication Data
US 2014/0100458 A1    Apr. 10, 2014

(30) Foreign Application Priority Data
Oct. 8, 2012 (KR) .......................... 10-2012-0111418

(51) Int. Cl.
*A61B 8/08*      (2006.01)
*A61B 8/00*      (2006.01)

(52) U.S. Cl.
CPC ............... *A61B 8/485* (2013.01); *A61B 8/4444* (2013.01); *A61B 8/4483* (2013.01); *A61B 8/54* (2013.01); *A61B 8/461* (2013.01); *A61B 8/5223* (2013.01)

(58) Field of Classification Search
CPC . G01S 7/2925; G01S 15/8927; A61B 8/4444; A61B 8/4483; A61B 8/485; A61B 8/5223; A61B 8/461; A61B 8/54
USPC ......................................................... 600/438
See application file for complete search history.

(56) References Cited

U.S. PATENT DOCUMENTS

| | | |
|---|---|---|
| 6,508,768 B1 | 1/2003 | Hall et al. |
| 7,252,004 B2 | 8/2007 | Fink et al. |
| 2010/0041995 A1 | 2/2010 | Fukukita et al. |
| 2011/0028838 A1 | 2/2011 | Pernot et al. |
| 2013/0317362 A1* | 11/2013 | Shi et al. ........................ 600/438 |

FOREIGN PATENT DOCUMENTS

WO     2011/153268     12/2011

\* cited by examiner

*Primary Examiner* — Katherine Fernandez
*Assistant Examiner* — Katherine McDonald
(74) *Attorney, Agent, or Firm* — Staas & Halsey LLP

(57) ABSTRACT

A method of measuring propagation of a shear wave by using an ultrasound transducer includes generating a shear wave inside the object, setting a region of interest (ROI) on which propagation of the shear wave is to be observed, and determining a position of a second focus on which ultrasound signals are to be directed to obtain information about the ROI, irradiating the ultrasound signals toward the second focus, and receiving echo signals reflected from the ROI.

22 Claims, 10 Drawing Sheets
(1 of 10 Drawing Sheet(s) Filed in Color)

METHOD, APPARATUS, AND SYSTEM FOR MEASURING PROPAGATION OF SHEAR WAVE USING ULTRASOUND TRANSDUCER

CROSS-REFERENCE TO RELATED APPLICATIONS

This application claims the priority benefit of Korean Patent Application No. 10-2012-0111418, filed on Oct. 8, 2012, in the Korean Intellectual Property Office, the disclosure of which is incorporated herein in its entirety by reference.

BACKGROUND

1. Field

The following description relates to a method, apparatus, and system for measuring a propagation of a shear wave by using an ultrasound transducer.

2. Description of the Related Art

Elastography technologies have been used to help make a medical diagnosis, for example, to measure mechanical properties of biological tissue, such as elasticity. Generally, the elastography technologies are additional features of conventional imaging aspects, such as Magnetic Resonance Imaging (MRI) or ultrasound waves, and are executed by medical imaging systems. In this regard, elastography gives additional clinical information to a doctor, thus helping the doctor to make a diagnosis.

SUMMARY

Additional aspects and/or advantages will be set forth in part in the description which follows and, in part, will be apparent from the description, or may be learned by practice of the invention.

Provided is a method, apparatus, and system for measuring propagation of a shear wave by using an ultrasound transducer.

Provided is a computer-readable recording medium having recorded thereon a program for executing the method on a computer.

Technical problems to be solved are not limited to the foregoing problems, and there may be other technical problems.

According to an aspect of the present disclosure, a method of analyzing elasticity information of a region of interest (ROI) in an object includes generating a shear wave inside the object, setting an ROI on which propagation of the shear wave is to be observed, and determining a position of a second focus on which ultrasound signals are to be directed to obtain information about the ROI, irradiating the ultrasound signals toward the second focus, and receiving echo signals reflected from the ROI.

According to an aspect of the present disclosure, a computer-readable recording medium has recorded thereon a program for executing the method of analyzing elasticity information of an ROI in an object on a computer.

According to an aspect of the present disclosure, an apparatus for analyzing elasticity information of an ROI in an object includes a second focus determining unit for determining a position of a second focus on which ultrasound signals are to be directed to obtain information about the ROI on which propagation of a generated shear wave is to be observed, a control unit for generating a control signal for irradiating the ultrasound signals onto the determined position of the second focus, an interface unit for receiving echo signals of the ultrasound signals which are irradiated toward the second focus and then reflected from the ROI, and an ultrasound image processing unit for obtaining the information about the ROI by using the received echo signals.

According to an aspect of the present disclosure, a system for analyzing elasticity information of an ROI in an object includes an ultrasound probe for generating a shear wave inside the object, irradiating ultrasound signals toward a second focus on which the ultrasound signals are to be directed to obtain information about the ROI on which propagation of a generated shear wave is to be observed, and receiving echo signals of the ultrasound signals which are reflected from the ROI, and a shear wave processing apparatus for determining a position of the second focus, generating a control signal for irradiating the ultrasound signals onto the determined position of the second focus, and obtaining information about the ROI by using the echo signals.

BRIEF DESCRIPTION OF THE DRAWINGS

The patent or application file contains at least one drawing executed in color. Copies of this patent or patent application publication with color drawings will be provided by the Office upon request and payment of the necessary fee. These and/or other aspects will become apparent and more readily appreciated from the following description of the embodiments, taken in conjunction with the accompanying drawings in which.

DETAILED DESCRIPTION

Hereinafter, embodiments of the present disclosure will be described with reference to the accompanying drawings.

Figure 1:
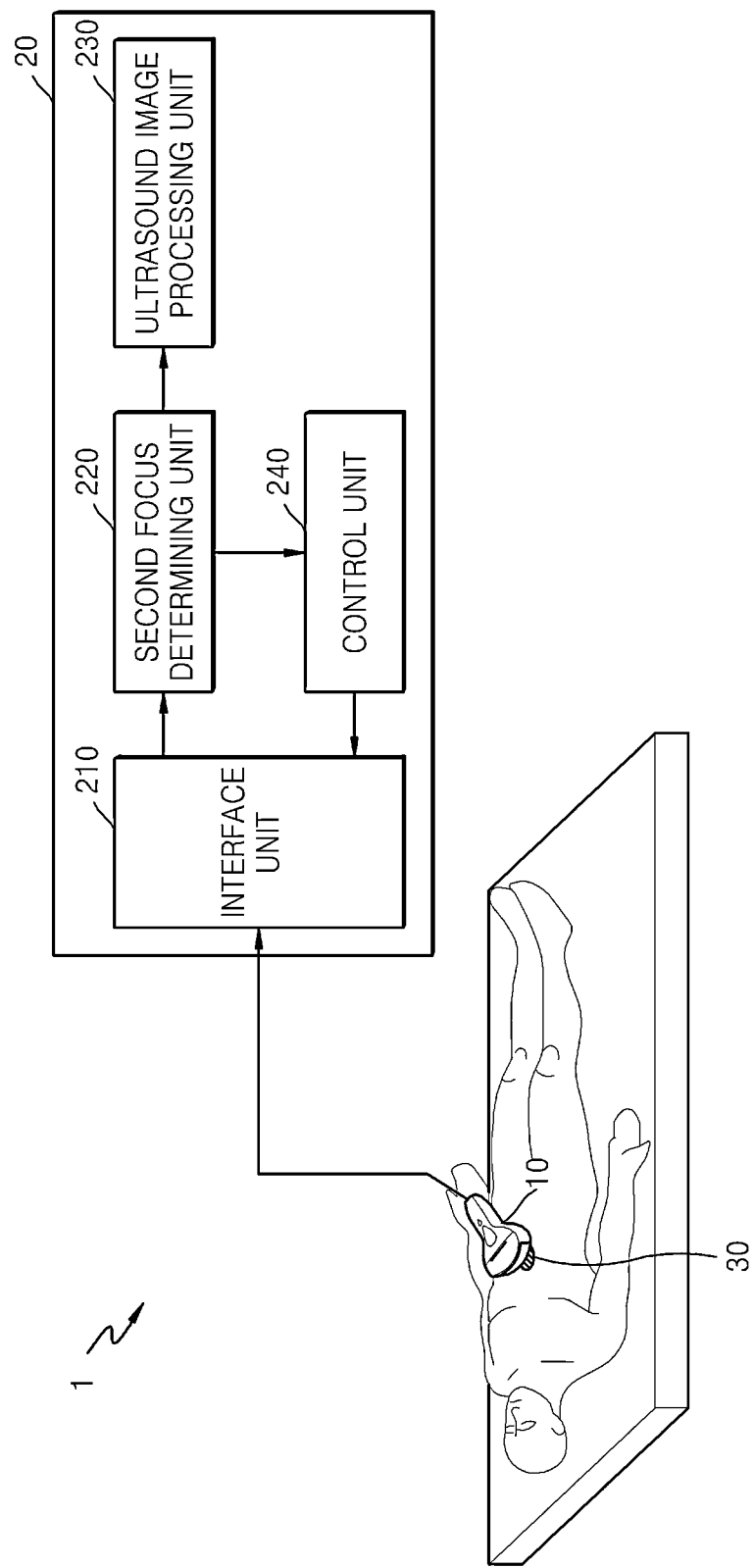
FIG. 1 is a diagram showing an example of a use environment of an elasticity analysis system according to an embodiment of the present disclosure.

FIG. 1 is a diagram showing an example of a use environment of an elasticity analysis system 1 according to an embodiment of the present disclosure.

Referring to FIG. 1, the elasticity analysis system 1 may include an ultrasound probe 10 and a shear wave processing apparatus 20, and the shear wave processing apparatus 20 may include an interface unit 210, a second focus determining unit 220, an ultrasound image processing unit 230, and a control unit 240.

The elasticity analysis system 1 of FIG. 1 is shown as including only components related to the current embodiment. However, those of ordinary skill in the art may understand that the elasticity analysis system 1 may further include general-purpose components in addition to the components shown in FIG. 1.

The interface unit 210, the second focus determining unit 220, the ultrasound image processing unit 230, and the control unit 240 shown in FIG. 1 may correspond to one processor or a plurality of processors. A processor may be implemented with an array of logic gates or may be implemented with a combination of a general-purpose microprocessor and a memory having stored therein a program which can be executed on the microprocessor. Those of ordinary skill in the art will understand that the processor can also be implemented with hardware.

The elasticity analysis system 1 according to the current embodiment analyzes the elasticity of tissue by using an ultrasound elastography technique to recognize a stiffness difference between normal tissue and abnormal tissue, and provide information for a user to make a diagnosis. Because the elasticity analysis system 1 according to the current embodiment analyzes the elasticity of tissue by using ultrasound waves, the elasticity analysis system 1 can be used to identify a state of tissue in a body, such as whether there is abnormal tissue like a cancer or a tumor, for example, or whether treatment has been completed when tissue is treated using high intensity focused ultrasound (HIFU).

For example, abnormal tissue has a difference in stiffness compared to normal tissue, and by analyzing the difference, the abnormal tissue may be identified. Thus, abnormal tissue such as a cancer or a tumor may have a higher elasticity than the normal tissue. For this reason, abnormal tissue such as a cancer or a tumor has a higher shear modulus than its neighboring normal tissue. When tissue is necrosed using a medical ultrasound wave such as HIFU, the elasticity of tissue increases as the necrosis of the tissue progresses. That is, a change in the state of the tissue may be represented by a change in the elasticity of the tissue. Therefore, by recognizing the elasticity of the tissue using the ultrasound wave, a user may non-invasively monitor the state of the tissue without directly observing the tissue in the body with the eyes.

The elasticity analysis system 1 provides a result of the analysis of the elasticity of the tissue by using an ultrasound image to thus be used to perform a diagnosis of a disease, treatment planning, or post-treatment assessment.

The ultrasound probe 10 generates shear waves inside an object. Hereinbelow, a point at which the ultrasound probe 10 generates the shear waves will be referred to as a first focus. The first focus may exist in, but not limited to, a region-of-interest (ROI) 30. Herein, the ROI 30 means a region in which a propagation of a shear wave is to be observed, and a region to which the ultrasound probe 10 is to irradiate an ultrasound signal. The first focus may refer to, but is not limited to, a lesion tissue whose treatment state is to be checked.

For example, prior to analysis of the elasticity of the tissue, the ultrasound probe 10 collects an ultrasound signal onto one or more points near the first focus to generate a shear wave on the first focus. To quantitatively analyze the elasticity by using the ultrasound signal, the ultrasound probe 10 may irradiate an Acoustic Radiation Force Impulse (ARFI) corresponding to the ultrasound signal according to the current embodiment into the body. As the shear wave is generated in the tissue by the irradiated ARFI, a displacement of the tissue may occur.

Figure 3:
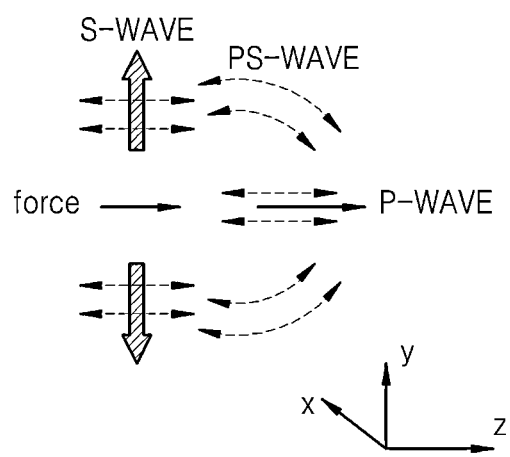
FIG. 3 is a diagram for describing a shear wave according to an embodiment of the present disclosure.

FIG. 3 is a diagram for describing a shear wave according to an embodiment of the present disclosure. Referring to FIG. 3, when a force of a point impulse is applied in a Z-axis direction, a P-wave, which is a longitudinal wave, an S-wave, which is a transverse wave, and a PS-wave, which is a result of coupling the two waves, are generated. Herein, the shear wave vibrates in a wave moving direction from a vibration source to which a force is applied, and propagates in a Y-axis direction, and the shear wave is an S-wave.

In the current embodiment, as a force of a point impulse for generating a shear wave, an ultrasound signal irradiated by the ultrasound probe 10 is assumed to be used. However, to generate a shear wave, a treatment ultrasound apparatus, such as an HIFU apparatus provided outside the elasticity analysis system 1 or a vibrator of an MRI apparatus, may also be used. That is, those of ordinary skill in the art understand that various means may be used to generate a shear wave on the first focus.

Referring back to FIG. 1, the ultrasound probe 10 irradiates ultrasound signals onto the ROI 30 including the first focus. Herein, the ROI 30 refers to a peripheral region including the first focus on which the shear wave is generated, and a region in which a propagation of the shear wave is to be observed. The ultrasound probe 10 irradiates ultrasound signals onto the ROI 30 and receives echo signals reflected from the ROI 30. The ROI 30 is a region included in an ultrasound image obtained by the ultrasound image processing unit 230 using the echo signals, and may be set as a region in which the shear wave generated by the ultrasound probe 10 maintains an amplitude at or above a predetermined level. For example, the ROI 30 may be set in the form of, but not limited to, a square with a 2 cm width and a 2 cm length, which has the first focus at its center. More specifically, the ROI 30 may be set in the form of a square, a circle, or other polygons. The ROI 30 may be set by the control unit 240 without a user's intervention based on the amplitude of the generated shear wave, and may be directly set by the user through the interface unit 210.

Figure 4A:
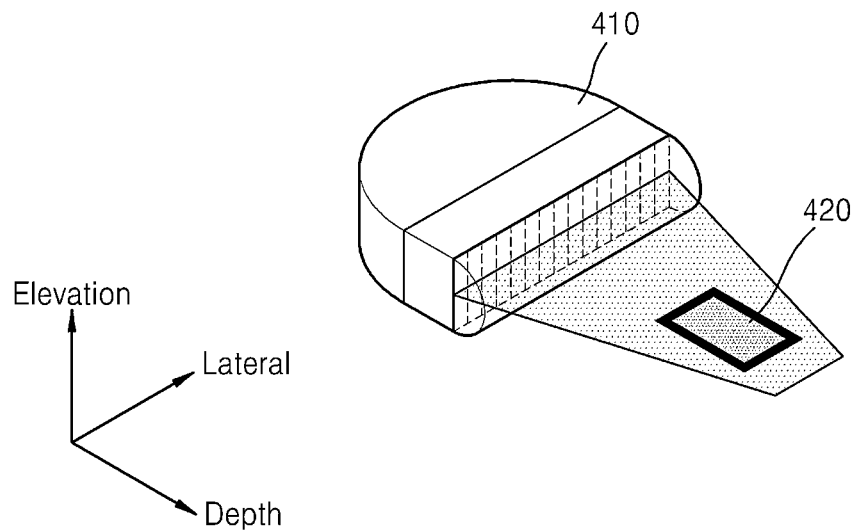
FIGS. 4A and 4B are diagrams showing an example in which an ultrasound probe irradiates ultrasound signals onto a region of interest, according to an embodiment of the present disclosure.
Figure 4B:
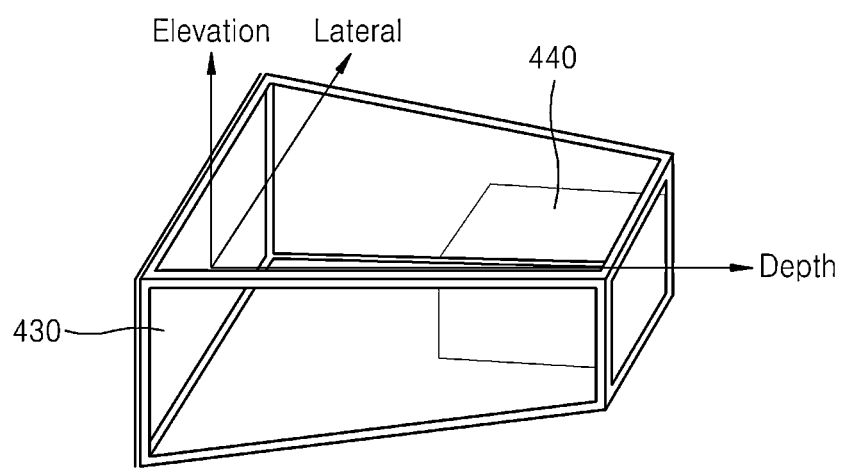

FIGS. 4A and 4B are diagrams showing an example in which the ultrasound probe 10 irradiates ultrasound signals onto the ROI 30, according to an embodiment of the present disclosure.

Referring to FIG. 4A, an ultrasound probe 410 may include a one-dimensional array of transducers. Herein, a transducer is an element of the ultrasound probe 410 that irradiates an ultrasound signal to an ROI 420 and receives echo signals reflected from the ROI 420. For example, if the transducer irradiates an ultrasound signal at 2-8 MHz to the ROI 420, the ultrasound signal is partially reflected from layers between several different tissues. The reflected echo signals vibrate the transducers. The transducers generate electrical pulses corresponding to vibration, and output the electrical pulses to the interface unit 210.

The transducers of the ultrasound probe 410 may form an aperture or a sub-array. Herein, the aperture refers to a set of some of the transducers of the ultrasound probe 410. However, the number of transducers of the aperture is not limited, and one transducer may form one aperture.

The ultrasound probe 410 collects ultrasound signals toward a second focus, and receives echo signals reflected from the ROI 420. Herein, the second focus refers to a focus on which the ultrasound probe 410 collects ultrasound signals, and the position of the second focus may be determined to be, but not limited to, outside the ROI 420. In particular, according to the current embodiment, the ultrasound signals irradiated by the ultrasound probe 410 are irradiated onto a region including the entire ROI 420. More specifically, the second focus according to the current embodiment may be determined by the second focus determining unit 220 such that the ultrasound signals are irradiated onto a region including the entire ROI 420, as shown in FIG. 4A. According to the current embodiment, the position of the second focus may be determined to be such that the ultrasound signals irradiated by the ultrasound probe 410 are uniformly irradiated onto the ROI 420.

In this way, the ultrasound probe 410 collects the ultrasound signals toward the second focus to thus improve a signal-to-noise ratio (SNR) of the echo signals received by the ultrasound probe 410. More specifically, if the ultrasound signals are irradiated without determining the second focus (e.g., if a plane wave is irradiated), the ultrasound signals may be irradiated onto the entire ROI 420, but the SNR of the echo signals is degraded and it may be difficult for the ultrasound signals to reach the ROI 420, which may be located deep inside the object. Therefore, as in the current embodiment, the ultrasound probe 410 collects the ultrasound signals toward the second focus, thereby improving the SNR of the echo signal and allowing the ultrasound signals to reach the ROI 420, which is located deep inside the object.

Referring to FIG. 4B, an ultrasound probe 430 may be formed as a two-dimensional (2D) array of transducers. The ultrasound probe 430 having the 2D array may irradiate ultrasound signals to a three-dimensional (3D) ROI 440 and receive echo signals reflected from the ROI 440. Herein, a process in which the ultrasound probe 430 irradiates ultrasound signals toward the second focus is as described above with reference to FIG. 4A.

Referring back to FIG. 1, the second focus determining unit 220 determines the position of the second focus outside the ROI 30 on which the ultrasound signals are to be directed by the ultrasound probe 10 to obtain the ultrasound image of the ROI 30. For example, the second focus determining unit 220 determines the position of the second focus on which the ultrasound signals are to be directed by the ultrasound probe 10, and transmits information about the position of the second focus to the control unit 240.

Figure 5:
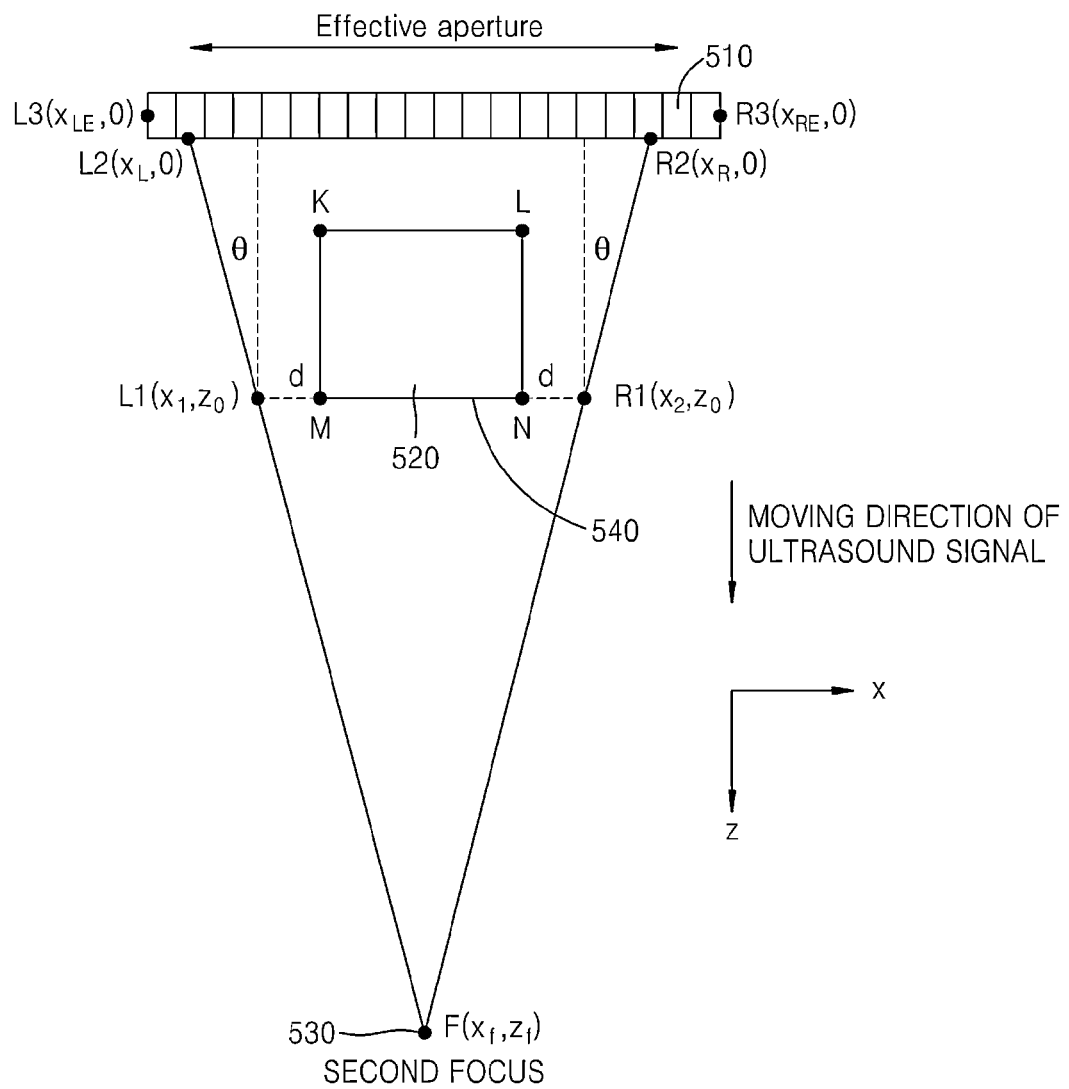
FIG. 5 is a diagram showing an example in which a second focus determining unit determines a position of a second focus, according to an embodiment of the present disclosure.

FIG. 5 is a diagram showing an example in which the second focus determining unit 220 determines the position of the second focus, according to an embodiment of the present disclosure.

Referring to FIG. 5, the position of a second focus 530 is determined to be such that ultrasound signals irradiated from the ultrasound probe 10 are irradiated onto a region including an entire ROI 520. More specifically, the position of the second focus 530 may be determined to be such that ultrasound signals irradiated by a plurality of transducers 510 of the ultrasound probe 10 are irradiated onto a region including the entire ROI 520. Herein, the ROI 520 may have the shape of a rectangle, a circle, or other polygons.

The second focus determining unit 220 may determine, as the second focus 530, an intersection of lines which connect two points located most distant from the first focus among a plurality of points forming the ROI 520 at each of both ends of an axis perpendicular to a moving direction of an ultrasound signal with each transducer located at each of both ends among the plurality of transducers 510 which irradiate the ultrasound signals. The second focus determining unit 220 may set a predetermined margin at each of the two points located most distant from the first focus in a direction away from the first focus, and determine, as the second focus 530, an intersection of lines connecting the two points with each of the transducers located at both ends among the plurality of transducers 510 which irradiate the ultrasound signals. Herein, the two points located most distant from the first focus may mean two points located most distant from the transducers among a plurality of points if there are points located most distant from the first focus at each of the both ends of the axis.

For the sake of convenience, assuming that the ROI 520 has the shape of a rectangle and the transducers 510 of the ultrasound probe 10 are arranged in a one-dimensional array, a detailed operation of the second focus determining unit 220 will be described.

The second focus determining unit 220 determines an edge which is most distant from the transducers 510 of the ultrasound probe 10 among a plurality of edges forming the ROI 520. For example, the second focus determining unit 220 may determine an edge 540 including vertexes M and N among four vertexes K, L, M, and N forming the ROI 520.

Thereafter, the second focus determining unit 220 sets a predetermined margin d along a direction perpendicular to a moving direction of an ultrasound signal from each of the both points of the determined edge 540 in a direction away from the first focus. Herein, the first focus is a position at which the ultrasound probe 10 generates a shear wave, and the ROI 520 may be set with respect to the first focus. The margin d may be set such that the ultrasound signals are uniformly irradiated to the ROI 520.

For example, the second focus determining unit 220 may set the margin d by using a wavelength of the ultrasound signal, a distance to the edge 540 from each transducer 510 which irradiates the ultrasound signal, or a combination of the wavelength and the distance. More specifically, the second focus determining unit 220 may set L1 and R1 at positions distanced by the margin d from the vertexes M and N in a direction away from the vertexes M and N. In the case that the ROI is a circle, a maximum distance point of the ROI that is furthest from the first focus along the circumference of the ROI may be determined. A maximum width of the ROI, such as the diameter of the circle along an axis perpendicular to a moving direction of the ultrasound signals, may be determined. For the circular ROI, L1 and R1 at positions distanced by the margin d plus one half of the maximum width at the maximum distance point, such that L1 and R1 lie on an axis tangent to the ROI at the maximum distance point, may be determined.

The second focus determining unit 220 may set the margin d by using:

$$d = \sqrt{\left(2z_0 + \frac{\lambda}{6}\right) \times \frac{\lambda}{6}} \qquad \text{[Equation 1]}$$

where $\lambda$ refers to a wavelength of an ultrasound signal irradiated by the transducer 510 of the ultrasound probe 10, and $z_0$ refers to a distance from the transducer 510 to the edge 540 including the vertexes M and N.

Generally, the wavelength of the ultrasound signal irradiated by the transducer 510 is much smaller than the distance from the transducer 510 to the edge 540 including the vertexes M and N, such that Equation 1 may be approximated to:

$$d \approx \sqrt{(2z_0) \times \frac{\lambda}{6}}$$ [Equation 2]

The second focus determining unit 220 applies the margin d, which is set using Equation 1 or Equation 2, to the vertexes M and N to determine the positions L1 and R1. Herein, the positions L1 and R1 may be indicated by coordinates with respect to an arbitrary origin which is set on an x-z plane, as shown in FIG. 5. For convenience, coordinates of the position L1 are expressed as $(x_1, z_0)$ and coordinates of the position R1 are expressed as $(x_2, z_0)$.

The second focus determining unit 220 determines the coordinates of the both ends of transducers which are to irradiate ultrasound signals among the transducers 510 of the ultrasound probe 10, by using coordinates of points set to have the margin d and an angle between a line perpendicular to each transducer 510 of the ultrasound probe 10 from each margin-set point, and a line connecting the second focus with each margin-set point. For example, the second focus determining unit 220 may determine positions L2 and R2 by using the coordinates of the positions L1 and R1 and an angle θ between each perpendicular line from each of the positions L1 and R1 to the transducers 510 and each line connecting the positions L1 and R1 with the positions L2 and R2.

Figure 6:
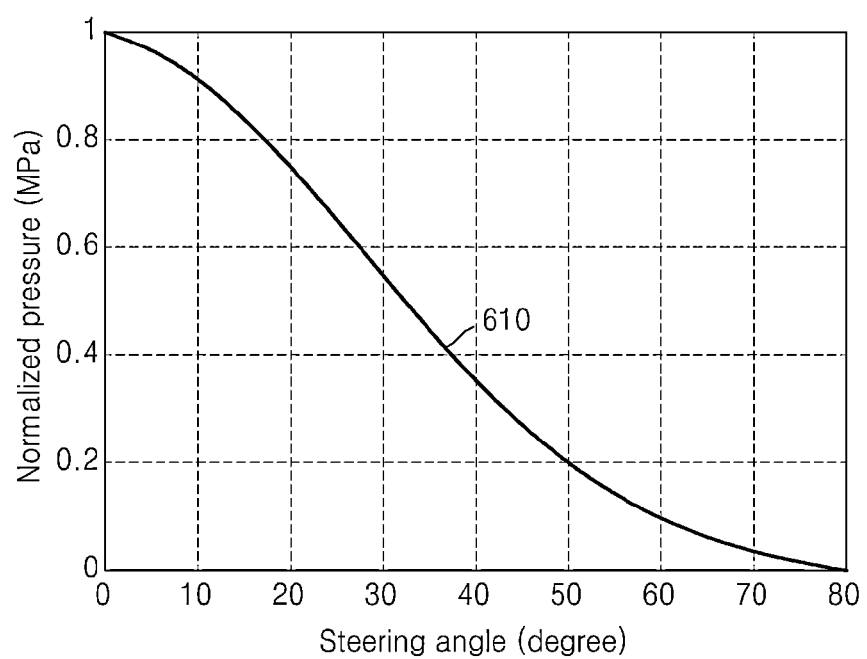
FIG. 6 is a graph showing a relationship between an angle θ and a normalized pressure according to an embodiment of the present disclosure.

Herein, angles θ between the perpendicular lines from the positions L1 and R1 to the transducers 510 and the lines connecting the positions L1 and R1 with the positions L2 and R2 may be previously set based on a level at which a pressure of an ultrasound signal irradiated from any one of the transducers 510 is measured at a position distanced by a predetermined distance from the transducer. For example, a relationship between the angle θ and a normalized pressure may be expressed as a curve 610 shown in FIG. 6.

The second focus determining unit 220 may determine an x-axis component $x_L$ of coordinates $(x_L, 0)$ corresponding to the position L2 by using:

$$x_L = x_1 - z_0 \tan(\theta)$$ [Equation 3]

wherein $x_1$ indicates an x-axis component of coordinates corresponding to the position L1, and $z_0$ indicates a z-axis component of the coordinates corresponding to the position L1. The angle θ refers to an angle between a perpendicular line from the position L1 to the transducers 510 and a line connecting the position L1 with the position L2. When the x-axis component $x_L$ calculated using Equation 3 results in an inward position of the left end of the transducers 510, that is, when $x_L$ is smaller than $x_{LE}$, the second focus determining unit 220 may replace $x_L$ with $x_{LE}$.

The second focus determining unit 220 may determine an x-axis component $x_R$ of coordinates $(x_R, 0)$ corresponding to the position R2 by using:

$$x_R = x_2 + z_0 \tan(\theta)$$ [Equation 4]

wherein $x_2$ indicates an x-axis component of coordinates corresponding to the position R1, and $z_0$ indicates a z-axis component of the coordinates corresponding to the position R1. The angle θ refers to an angle between a perpendicular line from the position R1 to the transducers 510 and a line connecting the position R1 with the position R2. When the x-axis component $x_R$ calculated using Equation 4 results in an inward position of the right end of the transducers 510, that is, when $x_{RE}$ is larger than $x_R$, the second focus determining unit 220 may replace $x_R$ with $x_{RE}$.

The second focus determining unit 220 determines the position of the second focus such that a boundary of a region onto which the ultrasound signals are irradiated intersects the two points which are set to have the margin d. For example, the second focus determining unit 220 may determine the position of the second focus by using the coordinates of the both ends of the transducers 510 and the coordinates of the margin-set points.

The second focus determining unit 220 may determine an x-axis component $x_f$ of coordinates $(x_f, z_f)$ indicating the position of the second focus 530 by using:

$$x_f = \frac{1}{x_R - x_L} \frac{x_1 x_R - x_2 x_L}{1 - \frac{x_2 - x_1}{x_R - x_L}}$$ [Equation 5]

wherein $x_1$ and $x_2$ indicate x-axis components of the positions L1 and R1, and $x_L$ and $x_R$ indicate x-axis components of the positions L2 and R2.

The second focus determining unit 220 may determine a z-axis component $z_f$ of coordinates $(x_f, z_f)$ indicating the position of the second focus 530 by using:

$$z_f = \frac{z_0}{1 - \frac{x_2 - x_1}{x_R - x_L}}$$ [Equation 6]

wherein $z_0$ indicates a distance from the transducers 510 to the edge 540 including the vertexes M and N. $x_1$ and $x_2$ indicate x-axis components of the positions L1 and R1, and $x_L$ and $x_R$ indicate x-axis components of the positions L2 and R2.

The second focus determining unit 220 transmits information about the position of the second focus 530 determined using Equations 1 through 6 to the control unit 240.

In the current embodiment, as the second focus determining unit 220 determines the position of the second focus, the ultrasound signals irradiated by the ultrasound probe 10 to obtain an ultrasound image of the ROI 520 may be concentrated on the ROI 520. Thus, the SNR of the echo signals may be improved and the ultrasound image processing unit 230 may more precisely obtain the ultrasound image of the ROI 520.

Referring back to FIG. 1, the control unit 240 generates a control signal for irradiating the ultrasound signals to the determined position of the second focus 530. For example, the control unit 240 generates a control signal of the ultrasound probe 10 for collecting the ultrasound signals toward the second focus 530 by using the information about the position of the second focus 530 transmitted from the second focus determining unit 220. The control unit 240 transmits the control signal to the interface unit 210.

The interface unit 210 receives echo signals, which are reflected signals of the ultrasound signals irradiated toward the second focus according to the control signal and then reflected from the ROI 30. For example, the interface unit 210 transmits the control signal transmitted from the second focus determining unit 220 to the ultrasound probe 10, and receives the echo signals from the ultrasound probe 10. Herein, the echo signals refer to reflected signals which are irradiated by the ultrasound probe 10 toward the second focus 530 and then reflected from the ROI 30. For example, the echo signals may be electric pulses generated by transducers of the ultrasound probe 10 in correspondence to the signals reflected from the ROI 30.

The interface unit 210 may be a unit which performs data input or output, or a unit which transmits user input information to other units. For example, the interface unit 210 may include input/output devices such as a display panel, a mouse, a keyboard, a touch screen, a monitor, or a speaker, for example, and software modules for driving them.

The ultrasound probe 10 irradiates the ultrasound signals toward the second focus 530. The ultrasound probe 10 receives the echo signals reflected from the ROI 30. For example, the ultrasound probe 10 controls the number of transducers which irradiate the ultrasound signals or a timing at which the respective transducers irradiate the ultrasound signals according to a position control signal transmitted from the control unit 240, irradiates the ultrasound signals toward the second focus 530, and receives the echo signals. The ultrasound probe 10 transmits the echo signals to the interface unit 210. Herein, a detailed algorithm for controlling the number of transducers which irradiate the ultrasound signals or a timing at which the transducers irradiate the ultrasound signals (that is, setting a timing at which each transducer irradiates the ultrasound signal) to collect the ultrasound signals to the second focus is obvious to those of ordinary skill in the art and thus will not be described in detail.

The ultrasound image processing unit 230 obtains information about the ROI 30 by using the received echo signals. The information about the ROI 30 may include beamformed radio frequency (RF) data or ultrasound images of the ROI 30.

For example, the ultrasound image processing unit 230 performs beamforming on the echo signals transmitted from the interface unit 210 with respect to the ROI 30, and obtains ultrasound images with respect to the ROI 30 by using the beamformed data. More specifically, the ultrasound image processing unit 230 may perform beamforming on the echo signals by using a timing at which respective transducers irradiate ultrasound signals, time instants at which the echo signals reach the transducers from the ROI 30, or a combination thereof.

Figure 7:
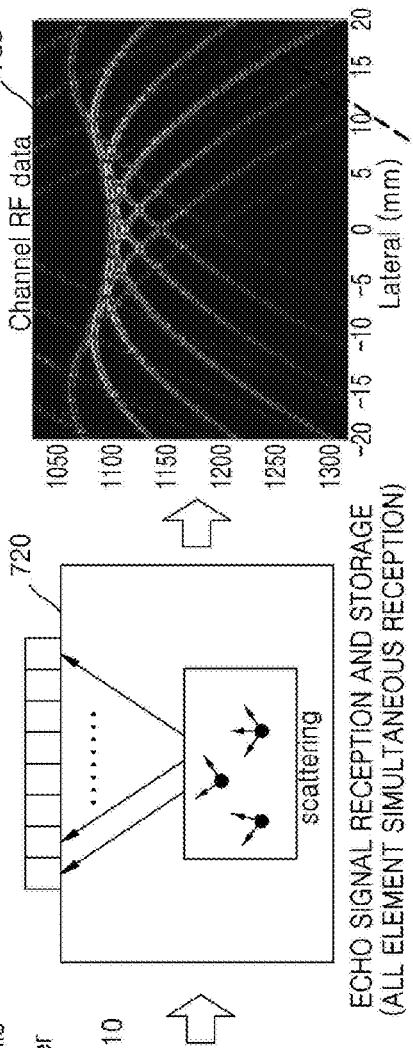
FIG. 7 is a diagram showing an example in which an ultrasound image processing unit performs beamforming processing on echo signals, according to an embodiment of the present disclosure.
Figure 7:
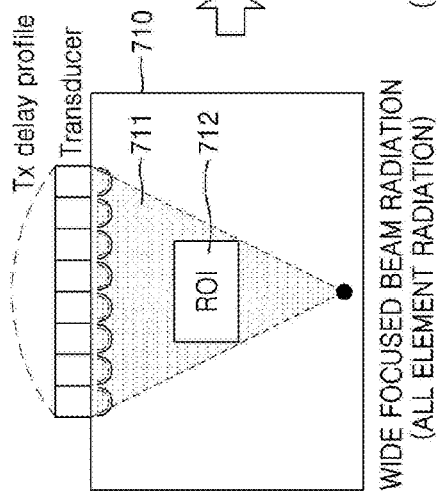
Figure 7:
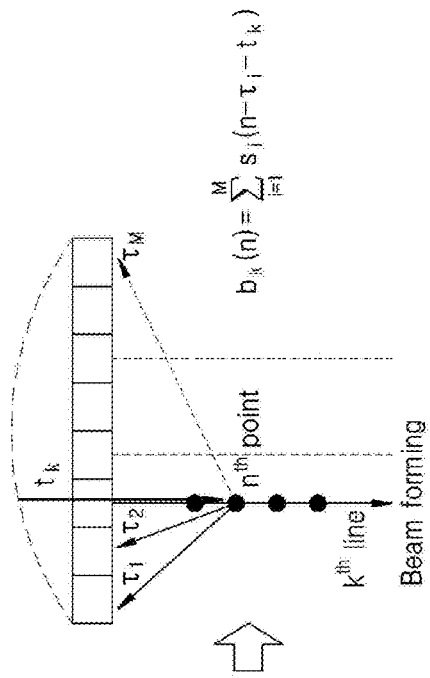

FIG. 7 is a diagram showing an example in which the ultrasound image processing unit 230 performs beamforming on echo signals, according to an embodiment of the present disclosure.

As indicated by 710 of FIG. 7, the transducers of the ultrasound probe 10 collect ultrasound signals on the second focus by using the position control signal transmitted from the control unit 240. As the transducers collect the ultrasound signals on the second focus, an ultrasound plane 711 formed by the ultrasound signals includes an entire ROI 712.

As indicated by 720 of FIG. 7, the transducers of the ultrasound probe 10 receive echo signals which are scattered and reflected from tissue in the ROI 712.

As indicated by 730 of FIG. 7, the ultrasound image processing unit 230 converts the echo signals into digital signals. Herein, each echo signal converted into a digital signal is referred to as channel RF data. The ultrasound image processing unit 230 transmits channel RF data to a storage unit (not shown). The ultrasound image processing unit 230 may convert the channel RF data into N RF frames (N is a natural number) and transmit them to the storage unit (not shown).

As indicated by 740 of FIG. 7, the ultrasound image processing unit 230 performs beamforming by using the channel RF data stored in the storage unit (not shown), thus obtaining the beamformed RF data. The ultrasound image processing unit 230 performs beamforming by using the channel RF data stored in the storage unit (not shown), thus obtaining the ultrasound image of the ROI 30. The ultrasound image processing unit 230 may also perform beamforming by using N RF frames stored in the storage unit (not shown), thus obtaining N ultrasound images with respect to the ROI 30. For example, the ultrasound image processing unit 230 may perform beamforming on the channel RF data by using:

$$b_k(n) = \sum_{i=1}^{M} S_i(n - \tau_i - t_k)$$ [Equation 7]

wherein $S_i$ indicates channel RF data which is a result of conversion of an echo signal received by an $i^{th}$ transducer, and $b_k$ indicates beamformed RF data on a $k^{th}$ line. $t_k$ indicates a time delay of irradiation of an ultrasound signal by a transducer to collect the ultrasound signal on the $k^{th}$ line, and $\tau_i$ indicates a time delay of an echo signal received by the $i^{th}$ transducer.

Figure 2:
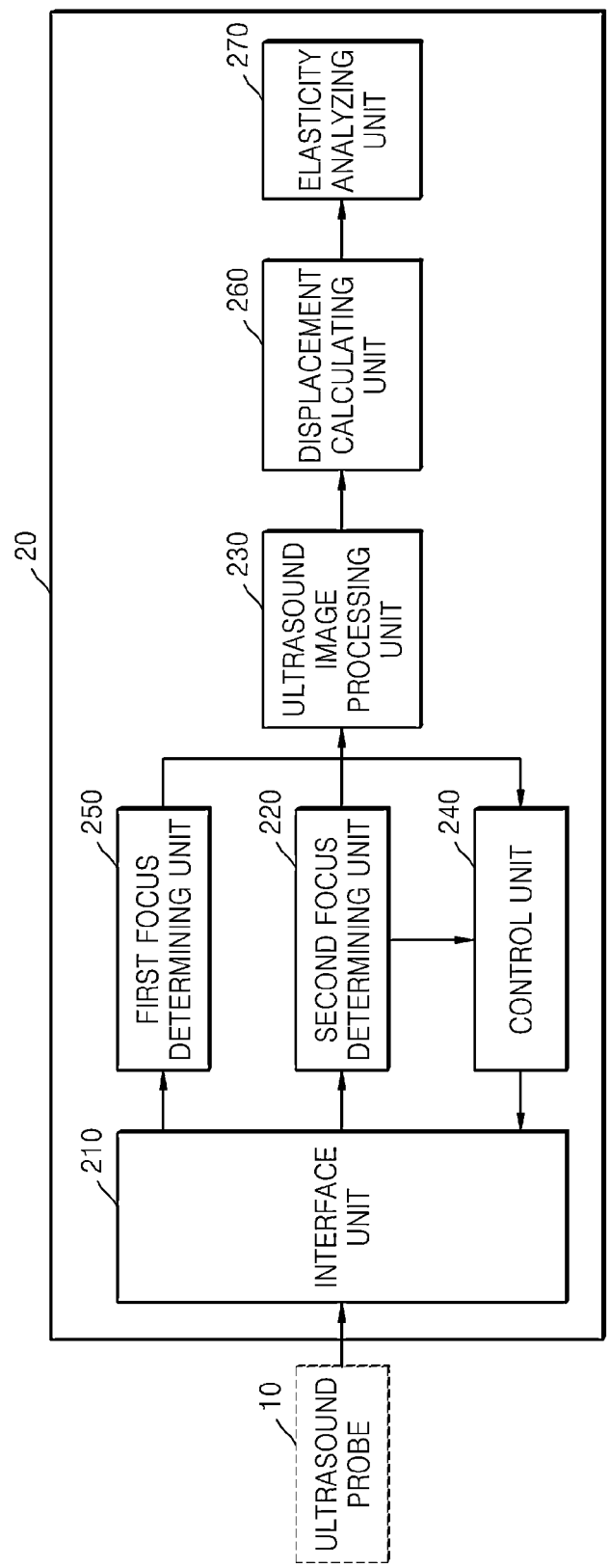
FIG. 2 is a diagram showing an example of a shear wave processing apparatus according to an embodiment of the present disclosure.

FIG. 2 is a diagram showing an example of the shear wave processing apparatus 20 according to an embodiment of the present disclosure.

Referring to FIG. 2, the shear wave processing apparatus 20 may include the interface unit 210, the second focus determining unit 220, the ultrasound image processing unit 230, the control unit 240, a first focus determining unit 250, a displacement calculating unit 260, and an elasticity analyzing unit 270.

In FIG. 2, only components of the shear wave processing apparatus 20, which are related to the current embodiment, are shown. Therefore, those of ordinary skill in the art understand that the shear wave processing apparatus 20 may further include general-purpose components in addition to the components shown in FIG. 2.

The interface unit 210, the second focus determining unit 220, the ultrasound image processing unit 230, the control unit 240, the first focus determining unit 250, the displacement calculating unit 260, and the elasticity analyzing unit 270 of the shear wave processing apparatus 20 shown in FIG. 2 may correspond to one processor or a plurality of processors. The processor may be implemented with an array of logic gates or may be implemented with a combination of a general-purpose microprocessor and a memory having stored therein a program which can be executed on the microprocessor. Those of ordinary skill in the art understand that the processor can also be implemented with hardware.

The operations of the interface unit 210, the second focus determining unit 220, the ultrasound image processing unit 230, and the control unit 240 of the shear wave processing apparatus 20 shown in FIG. 2 are as described above.

The first focus determining unit 250 determines the first focus, which is a point at which the ultrasound probe 10 is to generate a shear wave. Herein, the first focus may exist, but is not limited to, a point inside the ROI 30. The first focus may refer to, but is not limited to, tissue to be observed or its neighboring tissue. For example, the first focus determining unit 250 determines the position of the first focus, which is a point at which the ultrasound probe 10 is to generate a shear wave, and transmits information about the position of the first focus to the control unit 240. The position of the first focus may be determined by the first focus determining unit 250 without a user's intervention or may be determined directly by the user through the interface unit 210.

The displacement calculating unit 260 calculates a displacement of the shear wave based on a delay of beamformed data. For example, the displacement calculating unit 260 may receive beamformed RF data from the ultrasound image processing unit 230 and calculate a displacement of the shear wave based on the delay of the beamformed RF data. Because the beamformed RF data is obtained from the ultrasound image processing unit 230, a displacement of the shear wave calculated by the displacement calculating unit 260 corresponds to calculation of movement of the shear wave over time. That is, the calculated displacement of the shear wave has displacement components corresponding to an x axis, a y axis, or a z axis of an arbitrary coordinate space.

Because a general process of measuring a displacement of a shear wave based on a delay of beamformed RF data is obvious to those of ordinary skill in the art, a detailed algorithm will not be described.

The elasticity analyzing unit 270 analyzes elasticity information of tissue in the ROI 30 by using the calculated displacement of the shear wave. In the current embodiment, the analyzed elasticity information may include a shear modulus.

The elasticity analyzing unit 270 calculates a shear modulus of tissue in the ROI 30 by using displacement components corresponding to 2D coordinate axes (x axis and y axis) or 3D coordinate axes (x axis, y axis, and z axis) included in the calculated displacement of the shear wave. At this time, the elasticity analyzing unit 270 may calculate a shear modulus by using a wave equation regarding the shear wave. Hereinafter, the operation of the elasticity analyzing unit 270 will be described assuming that the displacement of the shear wave calculated by the displacement calculating unit 260 includes displacement components corresponding to respective 3D coordinate axes. If the displacement of the shear wave calculated by the displacement calculating unit 260 includes displacement components corresponding to respective 2D coordinate axes, the elasticity analyzing unit 270 may calculate a shear modulus by calculating a displacement component corresponding to the other axis using the displacement components corresponding to the respective 2D coordinate axes.

The elasticity analyzing unit 270 calculates a moving speed of the shear wave by using the displacement components corresponding to the respective 3D coordinate axes, which are included in the measured displacement of the shear wave.

$$\frac{\partial^2 u}{\partial t^2} = C_s^2 \cdot \left( \frac{\partial^2 u}{\partial x^2} + \frac{\partial^2 u}{\partial y^2} + \frac{\partial^2 u}{\partial z^2} \right) \quad \text{[Equation 8]}$$

where u indicates a displacement of a shear wave, and $C_S$ indicates a moving speed of the shear wave. While the elasticity analyzing unit 270 calculates the moving speed of the shear wave using Equation 8 in the current embodiment, the current embodiment is not limited thereto.

Next, the elasticity analyzing unit 270 calculates a shear modulus of tissue in the ROI 30 by using the calculated moving speed $C_S$ of the shear wave.

$$G = \rho \times C_s^2 \quad \text{[Equation 9]}$$

where G indicates a shear modulus and p indicates a density of a medium. The elasticity analyzing unit 270 has calculated the moving speed $C_S$ of the shear wave by using Equation 8 and ρ is an already-known value, such that the elasticity analyzing unit 270 may calculate the shear modulus G by using Equation 9. Although the elasticity analyzing unit 270 has calculated the shear modulus G by using Equation 9 in the current embodiment, the current embodiment is not limited thereto.

The elasticity analyzing unit 270 may also calculate the shear modulus G by using:

$$\rho \frac{\partial^2 u_z}{\partial t^2} = G(x, y, z) \left( \frac{\partial^2 u_z}{\partial x^2} + \frac{\partial^2 u_z}{\partial y^2} + \frac{\partial^2 u_z}{\partial z^2} \right) \quad \text{[Equation 10]}$$

$$\Leftrightarrow G(x, y, z) = \frac{\rho \frac{\partial^2 u_z}{\partial t^2}}{\frac{\partial^2 u_z}{\partial x^2} + \frac{\partial^2 u_z}{\partial y^2} + \frac{\partial^2 u_z}{\partial z^2}}$$

That is, the elasticity analyzing unit 270 may calculate the shear modulus G by using Equation 10, which is a combination of Equation 8 and Equation 9.

Figure 8:
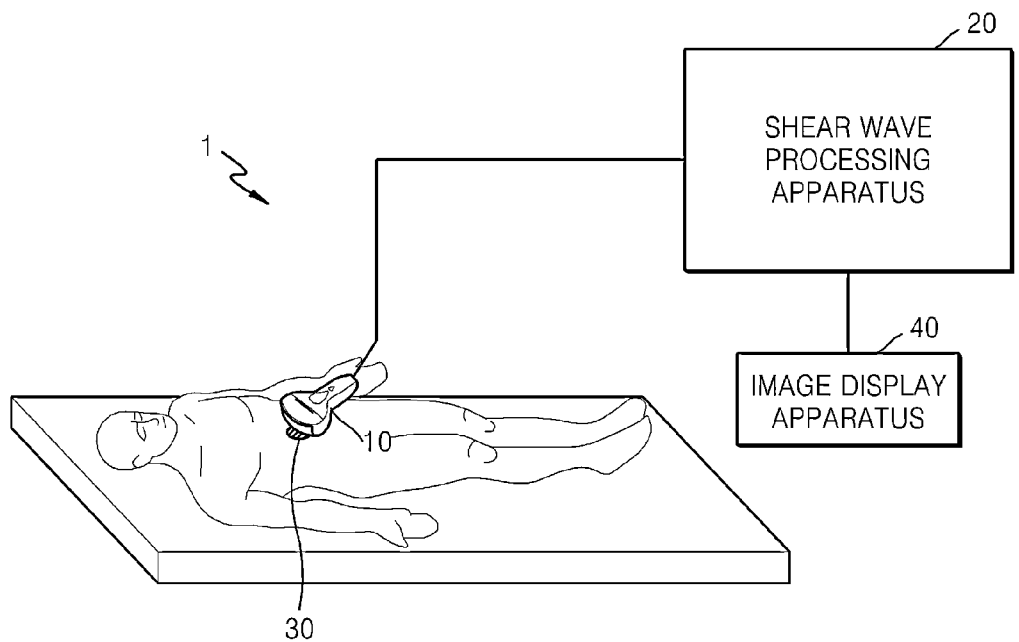
FIG. 8 is a diagram showing an example of a use environment of an elasticity analysis system according to an embodiment of the present disclosure.

As stated previously, the ultrasound image processing unit 230 obtains 3D ultrasound images of several tens of frames, and the displacement calculating unit 260 calculates the displacement of the shear wave, such that the elasticity analyzing unit 270 may calculate the shear modulus by considering all of the calculated displacement components. FIG. 8 is a diagram showing an example of a use environment of the elasticity analyzing system 1 according to an embodiment of the present disclosure. The elasticity analyzing system 1 according to the current embodiment includes the ultrasound probe 10, the shear wave processing apparatus 20, and an image display apparatus 40.

In FIG. 8, only components of the elasticity analyzing system 1, which are related to the current embodiment, are shown. Therefore, those of ordinary skill in the art understand that the elasticity analyzing system 1 may further include general-purpose components in addition to the components shown in FIG. 8.

The elasticity analyzing system 1 shown in FIG. 8 corresponds to an embodiment of the shear wave processing apparatus 20 shown in FIGS. 1 and 2. Therefore, descriptions related to FIGS. 1 and 2 are also applicable to the elasticity analyzing system 1 shown in FIG. 8 and thus are not repetitively provided.

The image display apparatus 40 displays an ultrasound image generated by the shear wave processing apparatus 20. For example, the image display apparatus 40 includes all output devices, such as a display panel, a mouse, a liquid crystal display (LCD) screen, or a monitor, for example, provided in the elasticity analyzing system 1.

Figure 9:
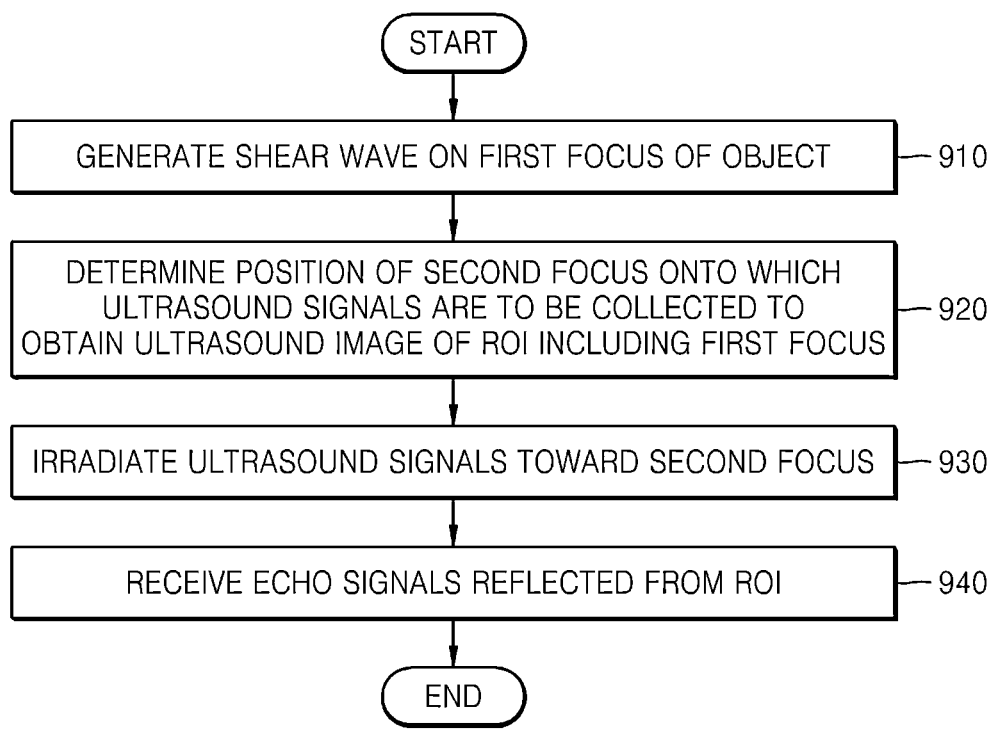
FIG. 9 is a flowchart showing a method of analyzing elasticity information of a region of interest in an object in a shear wave processing apparatus, according to an embodiment of the present disclosure.

FIG. 9 is a flowchart showing a method of analyzing elasticity information of an ROI in an object in the shear wave processing apparatus 20, according to an embodiment of the present disclosure. Referring to FIG. 9, the method includes operations which are time-serially processed by the shear wave processing apparatus 20 or the elasticity analyzing system 1 shown in FIGS. 1, 2, and 8. Therefore, although not provided below, the foregoing description of the shear wave processing apparatus 20 or the elasticity analyzing system 1 shown in FIGS. 1, 2, and 8 may also be applied to the method of FIG. 9.

In operation 910, the ultrasound probe 10 generates a shear wave inside an object. Herein, a point at which the ultrasound probe 10 generates the shear wave will be referred to as a first focus. The first focus may exist, but is not limited to, a point inside the ROI 30. Herein, the ROI 30 refers to a region in which a propagation of the shear wave is to be observed, and a region to which the ultrasound probe 10 is to irradiate an ultrasound signal. The first focus may refer to, but is not limited to, a lesion tissue whose treatment state is to be checked.

In operation 920, an ROI, on which the user is to observe propagation of the shear wave, is set through the control unit 240 or the interface unit 210, and the second focus determining unit 220 determines the position of the second focus on which ultrasound signals are to be directed to obtain an ultrasound image of the ROI 30. The position of the second focus is determined such that the ultrasound signals irradiated from the ultrasound probe 10 may be irradiated onto a region including the entire ROI 30. Herein, the ROI 30 may have the shape of a rectangle, as shown in FIG. 5, but may also have the shape of a circle or other polygons.

As the second focus determining unit 220 determines the position of the second focus, the ultrasound signals irradiated by the ultrasound probe 10 to obtain the ultrasound image of the ROI 30 may be concentrated on the ROI 30. Thus, the SNR of echo signals may be improved and the ultrasound image processing unit 230 may more precisely obtain the ultrasound image of the ROI 30.

In operation 930, the ultrasound probe 10 irradiates ultrasound signals toward the second focus.

In operation 940, the ultrasound probe 10 receives echo signals reflected from the ROI 30.

Figure 10:
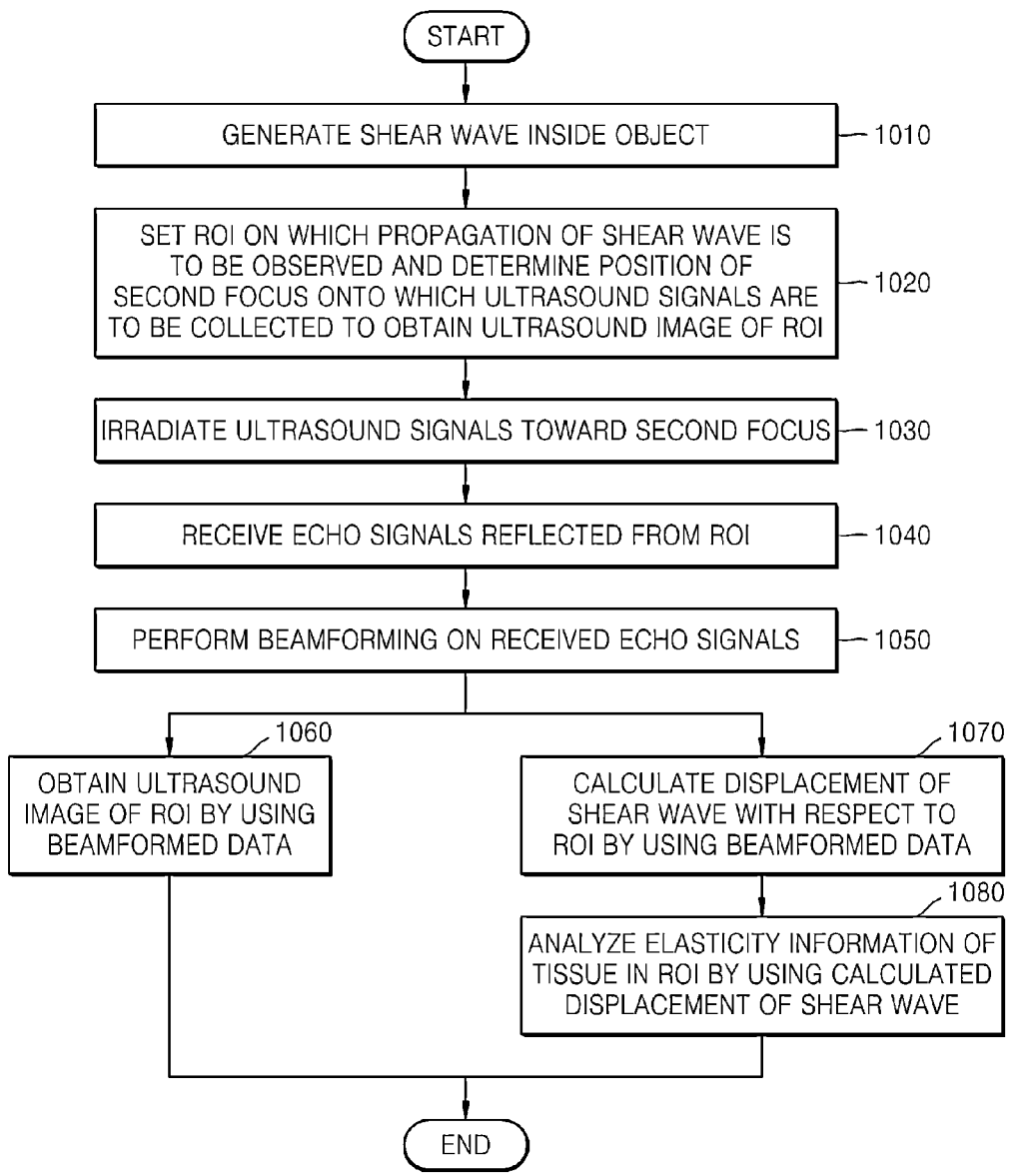
FIG. 10 is a flowchart showing an example of a method of analyzing elasticity information of a region of interest in an object in a shear wave processing apparatus, according to an embodiment of the present disclosure.

FIG. 10 is a flowchart showing an example of a method of analyzing elasticity information of an ROI in an object in the shear wave processing apparatus 20, according to an embodiment of the present disclosure. Referring to FIG. 10, the method includes operations which are time-serially processed by the shear wave processing apparatus 20 or the elasticity analyzing system 1 shown in FIGS. 1, 2, and 8. Therefore, although not provided below, the foregoing description of the shear wave processing apparatus 20 or the elasticity analyzing system 1 shown in FIGS. 1, 2, and 8 may also be applied to the method of FIG. 10.

Operations 1010 through 1040 correspond to operations 910 through 940 described with reference to FIG. 9, and thus are not described.

In operation 1050, the ultrasound image processing unit 230 performs beamforming on received echo signals. For example, the ultrasound image processing unit 230 may perform beamforming on the echo signals transmitted from the interface unit 210 on the ROI 30. More specifically, the ultrasound image processing unit 230 may perform beamforming on the echo signals by using a timing at which each transducer irradiates the ultrasound signal, a time instant at which the echo signals reach the transducers from the ROI 30, or a combination thereof.

In operation 1060, the ultrasound image processing unit 230 obtains the ultrasound image of the ROI 30 by using the beamformed data.

In operation 1070, the displacement calculating unit 260 calculates a displacement of the shear wave with respect to the ROI 30 by using the beamformed data. For example, the displacement calculating unit 260 may calculate the displacement of the shear wave based on a delay of the beamformed data of the received echo signals.

In operation 1080, the elasticity analyzing unit 270 analyzes elasticity information of tissue in the ROI 30 by using the calculated displacement of the shear wave. For example, the elasticity information analyzed by the elasticity analyzing unit 270 may include a shear modulus.

As the ultrasound probe 10 collects the ultrasound signals toward the second focus as in an embodiment of the present disclosure, the SNR of the echo signals received by the ultrasound probe 10 may be improved. More specifically, when the ultrasound signals are irradiated (e.g., a plane wave is irradiated) without determining the second focus, the ultrasound signals may be irradiated onto the entire ROI 30, but the SNR of the echo signal is degraded and it may be difficult for the ultrasound signals to reach the ROI 30, which is located deep inside the object. However, as in the current embodiment, the ultrasound probe 10 collects the ultrasound signals toward the second focus, thereby improving the SNR of the echo signal and allowing the ultrasound signals to reach the ROI 3, which is located deep inside the object.

In addition, the second focus determining unit 220 determines the second focus to uniformly irradiate the ultrasound signals onto the entire ROI, thereby improving the resolution of the ultrasound images obtained by the ultrasound image processing unit 230, regardless of the position of the ROI.

As described above, by collecting the ultrasound signals at the position of the second focus, the ultrasound signals may be irradiated uniformly over the entire ROI. Moreover, the ultrasound image may be obtained at a high speed according to the position change speed of the shear wave.

The ultrasound image can be obtained at a high speed according to the position change speed of the shear wave. The above-described embodiments may be recorded in computer-readable media including program instructions to implement various operations embodied by a computer. The media may also include, alone or in combination with the program instructions, data files, data structures, and the like. The program instructions recorded on the media may be those specially designed and constructed for the purposes of embodiments, or they may be of the kind well-known and available to those having skill in the computer software arts. Examples of computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. The computer-readable media may also be a distributed network, so that the program instructions are stored and executed in a distributed fashion. The program instructions may be executed by one or more processors. The computer-readable media may also be embodied in at least one application specific integrated circuit (ASIC) or Field Programmable Gate Array (FPGA), which executes (processes like a processor) program instructions. Examples of program instructions include both machine code, such as produced by a compiler, and files containing higher level code that may be executed by the computer using an interpreter. The above-described devices may be configured to act as one or more software modules in order to perform the operations of the above-described embodiments, or vice versa.

While the present disclosure has been particularly shown and described with reference to embodiments thereof, it will be understood by one of ordinary skill in the art that various changes in form and detail may be made therein without departing from the spirit and scope of the present disclosure as defined by the following claims. Accordingly, the disclosed embodiments should be considered in a descriptive sense and not in a restrictive sense. The scope of the present disclosure will be defined by the appended claims, and differences in scope equivalent to the appended claims should be construed as being included in the present disclosure.

What is claimed is:

1. A method comprising:
   generating a shear wave inside an object at a first focus;
   setting a region of interest (ROI) on which propagation of the shear wave is to be observed and at which the shear wave maintains an amplitude above a predetermined level;
   setting a margin based on a distance from a plurality of transducers of an ultrasound probe to the ROI and a wavelength of ultrasound signals to be irradiated by the plurality of transducers of the ultrasound probe;

setting, based on a width of the ROI and the margin, a position of a second focus on which the ultrasound signals are to be irradiated to obtain information about the ROI;

controlling the plurality of transducers of the ultrasound probe to irradiate the ultrasound signals toward the second focus; and receiving, by the plurality of transducers of the ultrasound probe, echo signals from the ultrasound signals irradiated toward the second focus and reflected from the ROI.

2. The method of claim 1, wherein the setting of the position of the second focus comprises setting, as the second focus, an intersection of lines that connect two points located most distant from the first focus among a plurality of points forming the ROI at each of both ends of an axis perpendicular to a moving direction of the ultrasound signals, and the first focus is a point at which the shear wave is generated.

3. The method of claim 2, wherein if there are a plurality of points located most distant from the first focus at each of the both ends of the axis, the two points located most distant from the first focus are two points most distant from the plurality of transducers among the plurality of points.

4. The method of claim 1, wherein the setting of the position of the second focus comprises setting, as the second focus, an intersection of lines connecting points, based on the margin in a direction away from the first focus from two points located most distant from the first focus among a plurality of points forming the ROI at each of both ends of an axis perpendicular to a moving direction of the ultrasound signals.

5. The method of claim 4, wherein the margin is set such that the ultrasound signals are uniformly irradiated onto the ROI.

6. The method of claim 1, wherein the setting of the position of the second focus comprises:

setting an edge located most distant from the plurality of transducers of the ultrasound probe among a plurality of edges forming the ROI;

setting the margin along a direction perpendicular to a moving direction of the ultrasound signals from each of both points of the set edge in a direction away from the first focus; and setting the position of the second focus such that a boundary of the region onto which the ultrasound signals are irradiated intersects the two points which are set to have the margin.

7. The method of claim 6, wherein the setting of the position of the second focus comprises:

setting coordinates of first and a second outer end of the plurality of transducers of the ultrasound probe, by using coordinates of points set to have the margin and an angle between a line perpendicular to the transducers of the ultrasound probe from each of the points set to have the margin, and a line which connects the second focus with both ends of the plurality of transducers of the ultrasound probe and passes through the points set to have the margin; and setting coordinates of the second focus by using the coordinates of the both ends of the plurality of transducers and coordinates of the points set to have the margin.

8. The method of claim 1, wherein the irradiating of the ultrasound signals toward the second focus comprises irradiating the ultrasound signals toward the second focus by controlling a number of transducers of the plurality of transducers which irradiate the ultrasound signals, calculated according to the position of the second focus, or a timing at which each transducer of the plurality of transducers irradiates the ultrasound signals.

9. The method of claim 1, further comprising performing beamforming on the received echo signals on the ROI and obtaining ultrasound images of the ROI by using the beamformed data.

10. The method of claim 9, wherein the beamforming is performed by using a timing at which each transducer of the plurality of transducers irradiates the ultrasound signals, a time instant at which the echo signals reach the plurality of transducers from the ROI, or a combination thereof.

11. The method of claim 1, wherein the setting of the position of the second focus comprises:

setting the first focus comprising an axis perpendicular to the moving direction of the ultrasound signals where the ultrasound signals are generated;

setting a maximum width of the ROI along an axis perpendicular to a moving direction of the ultrasound signals;

setting a maximum distance point of the ROI that is furthest from the first focus;

setting a first point on a left side of the ROI along an axis perpendicular to the moving direction of the ultrasound signals which passes through the maximum distance point, and at a distance from a centerline of the ROI equal to one half the maximum width plus the margin;

setting a second point on a right side of the ROI along an axis perpendicular to the moving direction of the ultrasound signals which passes through the maximum distance point, and at a distance from a centerline of the ROI equal to one half the maximum width plus the margin; and setting the position of the second focus to be the point where a first line originating at a left side of the first focus and passing through the first point intersects a second line originating at a right side of the first focus and passing through the second point.

12. The method of claim 11, wherein the origination points of the first line and the second line are set based on a level at which a pressure of an ultrasound signal is measured at a position a predetermined distance from a point where the ultrasound signals are generated.

13. The method of claim 11, wherein the origination points of the first line and the second line are set based on a left endpoint of the first focus and a right endpoint of the first focus, respectively.

14. A non-transitory computer-readable recording medium storing one or more programs to implement a method comprising:

generating a control signal to generate a shear wave inside an object at a first focus;

setting a region of interest (ROI) on which propagation of the shear wave is to be observed and at which the shear wave maintains an amplitude above a predetermined level;

setting a margin based on a distance from a plurality of transducers of an ultrasound probe to the ROI and a wavelength of ultrasound signals to be irradiated by the plurality of transducers of the ultrasound probe;

setting, based on a width of the ROI and the margin, a position of a second focus on which the ultrasound signals are to be irradiated to obtain information about the ROI;

generating a control signal to irradiate, by the plurality of transducers of the ultrasound probe, the ultrasound signals toward the second focus; and generating a control signal to receive, by the plurality of transducers of the ultrasound probe, echo signals from the ultrasound signals irradiated toward the second focus and reflected from the ROI.

15. An apparatus comprising:
a second focus setting unit for setting a margin based on a distance from a plurality of transducers of an ultrasound probe to a region of interest (ROI) and a wavelength of ultrasound signals to be irradiated by the plurality of transducers of the ultrasound probe, and setting, based on a width of the ROI and the margin, a position of a second focus on which the ultrasound signals are to be irradiated to obtain information about the ROI on which propagation of a generated shear wave is to be observed and at which the shear wave maintains an amplitude above a predetermined level;
a control unit for generating a control signal for irradiating, using the plurality of transducers of the ultrasound probe, the ultrasound signals onto the set position of the second focus;
a receiver for receiving echo signals of the ultrasound signals which are irradiated toward the second focus and then reflected from the ROI; and
an ultrasound image processing unit for obtaining the information about the ROI by using the received echo signals.

16. The apparatus of claim 15, wherein the second setting unit sets, as the second focus, an intersection of lines that connect two points located most distant from the first focus among a plurality of points forming the ROI at each of both ends of an axis perpendicular to a moving direction of the ultrasound signals, and the first focus is a point at which the shear wave is generated.

17. The apparatus of claim 16, wherein the two points located most distant from the first focus are two points set to have the margin in a direction away from the first focus.

18. The apparatus of claim 17, wherein the margin is set such that the ultrasound signals are uniformly irradiated onto the ROI.

19. The apparatus of claim 15, wherein the second focus setting unit sets, as the second focus, an intersection of lines connecting points, which have the margin in a direction away from the first focus from two points located most distant from the first focus among a plurality of points forming the ROI at each of both ends of an axis perpendicular to a moving direction of the ultrasound signals.

20. The apparatus of claim 15, wherein the ultrasound image processing unit irradiates the ultrasound signals toward the second focus by controlling a number of transducers of the plurality of transducers which irradiate the ultrasound signals or a timing at which each transducer of the plurality of transducers irradiates the ultrasound signals, and receives echo signals.

21. The apparatus of claim 15, further comprising a displacement setting unit for performing beamforming on the received echo signals on the ROI and setting a displacement of the shear wave based on a delay of beamformed waveforms.

22. A system comprising:
an ultrasound probe for generating a shear wave inside an object at a first focus, including a plurality of transducers for irradiating ultrasound signals toward a second focus on which the ultrasound signals are to be irradiated to obtain information about a region of interest (ROI) on which propagation of a generated shear wave is to be observed and at which the shear wave maintains an amplitude above a predetermined level, and receiving echo signals of the ultrasound signals which are irradiated toward the second focus and reflected from the ROI; and
a shear wave processing apparatus for setting a margin based on a distance from the plurality of transducers of the ultrasound probe to the region of interest (ROI) and a wavelength of the ultrasound signals irradiated by the plurality of transducers of the ultrasound probe, for setting, based on a width of the ROI and the margin, a position of the second focus, generating a control signal for the irradiating, using the plurality of transducers of the ultrasound probe, the ultrasound signals onto the set position of the second focus, and obtaining the information about the ROI by using the echo signals.

* * * * *